United States Patent
Nord et al.

(10) Patent No.: US 8,009,802 B2
(45) Date of Patent: Aug. 30, 2011

(54) METHOD AND APPARATUS TO FACILITATE SUPPLEMENTING A DOSE-VOLUME HISTOGRAM CONSTRAINT USING AN ADAPTIVE DOSE-VOLUME HISTOGRAM CONSTRAINT

(75) Inventors: Janne Nord, Espoo (FI); Jarkko Peltola, Tuusula (FI)

(73) Assignee: Varian Medical Systems International AG, Zug (CH)

( * ) Notice: Subject to any disclaimer, the term of this patent is extended or adjusted under 35 U.S.C. 154(b) by 0 days.

(21) Appl. No.: 12/564,488

(22) Filed: Sep. 22, 2009

(65) Prior Publication Data
US 2011/0069815 A1   Mar. 24, 2011

(51) Int. Cl.
*A61N 5/10* (2006.01)
(52) U.S. Cl. .......................................... 378/65
(58) Field of Classification Search ............ 378/65
See application file for complete search history.

(56) References Cited

U.S. PATENT DOCUMENTS

| 7,162,008 | B2 | 1/2007 | Earl et al. | |
|---|---|---|---|---|
| 7,333,591 | B2 | 2/2008 | Earl et al. | |
| 2004/0071261 | A1* | 4/2004 | Earl et al. | 378/65 |
| 2006/0256915 | A1 | 11/2006 | Otto et al. | |
| 2008/0152085 | A1* | 6/2008 | Saracen et al. | 378/65 |
| 2008/0226030 | A1 | 9/2008 | Otto | |
| 2008/0298550 | A1 | 12/2008 | Otto | |

FOREIGN PATENT DOCUMENTS

| WO | 2008011725 A1 | 1/2008 |
|---|---|---|
| WO | 2008130634 A1 | 10/2008 |

OTHER PUBLICATIONS

Wang et al., "Arc-Modulated Radiation Therapy (AMRT): A Single Arc Form of Intensity-Modulated Arc Therapy," Physics in Medicine and Biology 53 (2008); 13 pages; IOP Publishing.

* cited by examiner

*Primary Examiner* — Glen Kao
(74) *Attorney, Agent, or Firm* — Fitch Even Tabin & Flannery

(57) ABSTRACT

One provides a first dose-volume histogram (DVH) constraint as pertains to controlling localized excessive-radiation dosage with respect to a particular treatment volume. One then automatically determines whether to supplement this constraint by using an adaptive DVH constraint. These teachings will accommodate determining whether to supplement the first DVH constraint, at least in part, by determining whether a user has specified such supplementation (using, for example, a corresponding user interface) by, for example, placing at least one DVH constraint such that the constraint corresponds to a volume fraction at a range boundary.

20 Claims, 1 Drawing Sheet

METHOD AND APPARATUS TO FACILITATE SUPPLEMENTING A DOSE-VOLUME HISTOGRAM CONSTRAINT USING AN ADAPTIVE DOSE-VOLUME HISTOGRAM CONSTRAINT

TECHNICAL FIELD

This invention relates generally to radiation-treatment planning and more particularly to the use of dose-volume histograms.

BACKGROUND

The use of radiation to treat various illnesses and maladies comprises a known area of endeavor. A corresponding radiation-treatment plan typically informs and guides the administration of radiation for such purposes. These plans often serve to provide a therapeutically-useful dose to a given treatment volume (such as, for example, a tumor) while attempting to minimize dosing non-targeted regions (such as adjacent healthy tissue) beyond some threshold. Dose-volume histograms (frequently denoted by the acronym "DVH") are often employed to inform the development of such radiation-treatment plans.

It is also known that hot and cold spots (i.e., areas where dosing is "excessive" in that the dosing is either too much or inadequate, respectively) can occur in practice. The location and size of such spots typically depends, at least in part, upon geometric and dosimetric constraints as pertain to a given optimized application setting. Hot and cold spots are undesirable. Dose-volume histogram constraints are often employed to attempt to minimize the occurrence or severity of hot and cold spots. For example, traditional dose-volume histogram constraints penalize the objective function when a particular volume fraction is exceeded at a given dose. Unfortunately, volume fraction and dosing are often difficult to accurately predict in many application settings.

As a result, it remains a difficult challenge to adequately control hot and cold spots using traditional approaches. If the constraint is set too tightly (regarding weight and/or volume percentages) other aspects of the treatment can suffer. Conversely, if the constraint is set too loosely, hot or cold spots can appear.

BRIEF DESCRIPTION OF THE DRAWINGS

The above needs are at least partially met through provision of the method and apparatus to facilitate supplementing a dose-volume histogram constraint using an adaptive dose-volume histogram constraint described in the following detailed description, particularly when studied in conjunction with the drawings, wherein.

Figure 1:
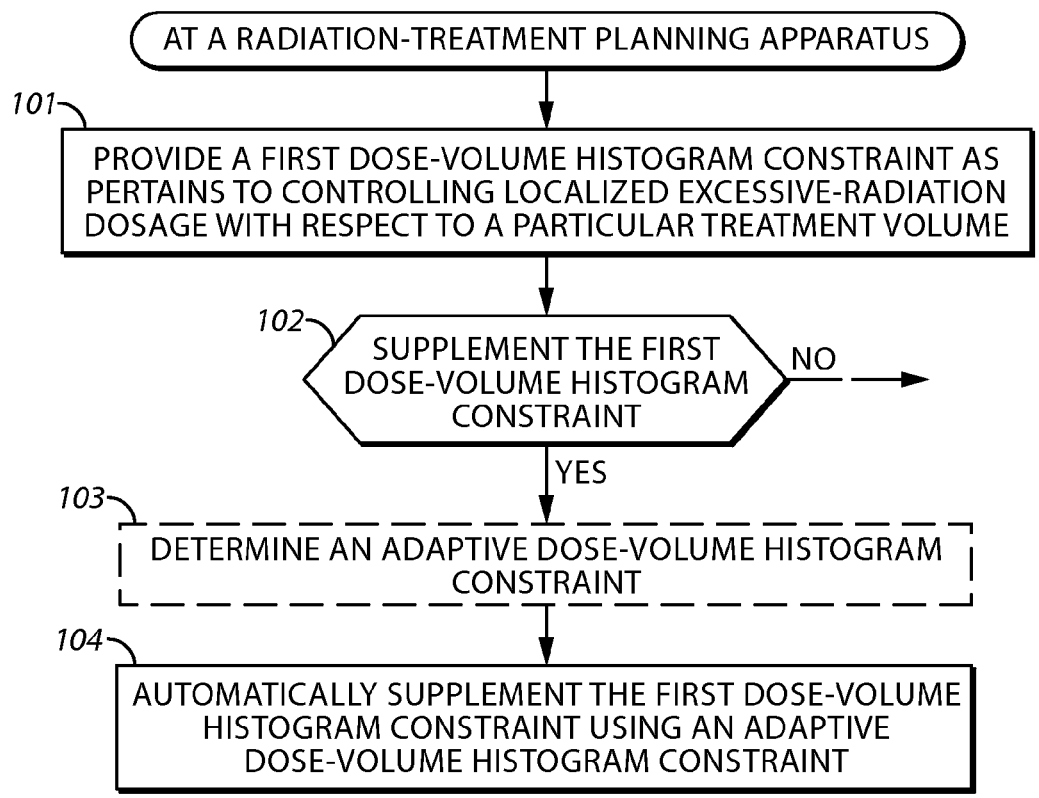
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, one can provide a first dose-volume histogram constraint as pertains to controlling localized excessive-radiation dosage with respect to a particular treatment volume. One can then automatically determine whether to supplement this first dose-volume histogram constraint. When supplementing, one can then automatically supplement the first dose-volume histogram constraint using an adaptive dose-volume histogram constraint.

By one approach, one can determine the first dose-volume histogram constraint by penalizing and/or emphasizing a corresponding objective function when at least one identified volume fraction is exceeded at a given radiation dosage. This emphasis can comprise, for example, ensuring that a target region (such as a tumor) receives at least sixty Gy.

These teachings will also accommodate determining whether to supplement the first dose-volume histogram constraint, at least in part, by determining whether a user has specified such supplementation (using, for example, a corresponding user interface) by, for example, placing at least one dose-volume histogram constraint such that the constraint corresponds to a volume fraction at a range boundary.

If desired, the referred-to activity of supplementing the first dose-volume histogram constraint can comprise penalizing no more than a predefined volume fraction that is smaller than the volume fraction that is constrained by the first dose-volume histogram constraint. For example, by one approach, this predefined volume fraction might be no more than about 1.0% of the treatment volume, 0.1% of the treatment volume, and so forth.

These teachings are readily applied in conjunction with various radiation-treatment platforms. For example, these teachings can be used with an arc-radiation treatment-planning apparatus. As another example, these teachings can be used with an intensity-modulated radiation-treatment planning apparatus.

So configured, these teachings facilitate the reduction of hot spots and/or cold spots. Those skilled in the art will appreciate that these results are attainable without necessarily requiring size, location, or dose information prior to beginning optimization. This proves very useful in practice because such information is often difficult to know prior to optimization. These benefits arise in part by employing an adaptive dose-volume histogram-based constraint that tends to only penalize for a predefined lowest proportion (and/or for a predefined highest portion, as desired) of the dose-volume histogram curve.

Those skilled in the art will also appreciate that these teachings will readily accommodate a useful, corresponding user interface. By one approach, for example, dose-volume histogram dose-percentage constraints that are set to 0% or 100% via such an interface can be usefully interpreted as including hot or cold spot contributions.

These and other benefits may become clearer upon making a thorough review and study of the following detailed description. Referring now to the drawings, and in particular to FIG. 1, an illustrative process 100 that is compatible with many of these teachings will now be presented. This process 100 can be carried out in conjunction with a radiation-treatment planning apparatus of choice. This can comprise, as one example, an arc-radiation treatment-planning apparatus. As another example, this can comprise an intensity-modulated radiation-treatment planning apparatus. Such apparatuses are known in the art and require no further elaboration here.

This process 100 includes the step 101 of providing a first dose-volume histogram constraint as pertains to controlling localized excessive-radiation dosage with respect to a particular treatment volume. (As used herein, the expression "excessive-radiation dosage" will be understood to refer to a dosage that is inappropriately too much or too little.) This control generally comprises reducing the local dosage when dealing with a hot spot and increasing the local dosage when dealing with a cold spot. Those skilled in the art will be well familiar with dose-volume histograms and their use in radiation treatment planning. Generally speaking, a dose-volume histogram serves to represent or summarize three-dimensional dose distributions in a graphical two-dimensional format. The "volume" referred to in a dose-volume histogram analysis can be the radiation-treatment target, a nearby healthy organ, some arbitrary structure, or the like. Clinically-used dose-volume histogram's usually present all structures and targets of interest in the treatment volume, with each line comprising a different color and representing a different structure.

This first dose-volume histogram constraint can comprise a constraint as is traditionally calculated in these regards. Such a constraint serves to penalize the objective function when a certain volume fraction is exceeded at a certain dose. As this comprises a well-understood area of endeavor, further elaboration will not be presented here in these regards aside from noting that accurately predicting the volume fraction and dose values often proves challenging, hence rendering it difficult to control hot and cold spots with this first dose-volume histogram constraint.

This process 100 then provides the step 102 of automatically determining whether to supplement this first dose-volume histogram constraint. This determination can be based, by one approach, upon determining whether a user has specified such supplementation. A user interface of choice can serve to provide such an indication. By one approach, for example, a graphical user interface (such as a display of choice) can present a dose-volume histogram to be viewed by the user. This process can then detect when the user places one or more dose-volume histogram constraints (using, for example, a cursor-control mechanism of choice) with respect to that dose-volume histogram such that the constraint corresponds to a volume fraction at a range boundary. For example, a range boundary can comprise 0%, 100%, or both such values.

By using such an approach, this process 100 can automatically determine to supplement the aforementioned first dose-volume histogram constraint as a function, at least in part, of inputs provided by the user regarding the placement of dose-volume histogram constraints at a range boundary. Depending upon the requirements and/or opportunities as tend to characterize a given application settings, this determination can be based, in whole or in part, upon such other criteria as may be of interest. (In the absence of such a determination, those skilled in the art will understand that this process 100 can continually loop through this step, if desired, or can temporarily jump elsewhere within the process 100 (or to another process) as desired. This step can also comprise an interrupt-based capability as is known in the art if desired.)

As illustrated in FIG. 1 by the use of phantom lines, this process 100 will accommodate the optional step 103 of determining an adaptive dose-volume histogram constraint. Examples in this regard are provided below.

In any event, regardless of how one determines or provides this adaptive dose-volume histogram constraint, this process 100 employs the step 104 of automatically supplementing the first dose-volume histogram constraint using an adaptive dose-volume histogram constraint. This can comprise, for example, further penalizing no more than a predefined volume fraction that is smaller than the volume fraction that is constrained by the first dose-volume histogram constraint. This predefined volume fraction might comprise, for example, no more than about 1.0% of the treatment volume. As another example, this predefined volume fraction might comprise no more than about 0.1% of the treatment volume. (As used herein, the expression "predefined" will be understood to refer to a determination that well precedes, both in time and in terms of executed functionality, the point in time when the corresponding value is utilized as described. A determination that occurs during the course of this described process, then, does not comprise a predefinition by this point of view.)

Using such an approach, and by way of illustration and with no intent of suggesting limitations in these regards, only the predefined volume fraction will be penalized by the constraint to control a hot spot. By limiting the penalization to only this small fraction of the overall volume, the weight does not become too high and then prevent other useful optimization tradeoffs. As a result, a higher penalty can be employed for the affected region to thereby better control the hot spot without also unduly disrupting dosing elsewhere in the treatment volume. As one simple example in these regards, (dose at the point of interest−constraint dose)$^3$ could be used instead of (dose at the point of interest−constraint dose)$^2$.

As a related example pertaining to controlling a cold spot, a higher fraction (such as, for example, 99.9%) could be defined such that only the fraction exceeding the predefined value is penalized.

EXAMPLE 1

By way of illustration and without intending any limitations in these regards, in a first example, a target may have a user-defined objective to receive less than a 60 Gy dose. Using this 60 Gy value, a threshold value can be calculated. For example, increasing this amount by 5% will yield a value of 63 Gy for the adaptive constraint. In practice, this 60 Gy limit might not be possible in all instances due to other constraints. For example, a 1.0% fraction of the target may receive 62 Gy while a 0.1% fraction of the target might receive a dose exceeding 65 Gy. The predefined maximum fraction for the adaptive constraint could be set at 0.2%. In this case, then, the amount exceeding the threshold value of 63 Gy could be 0.15% and the adaptive constraint would then be applied to this 0.15% fraction of the region (but not elsewhere).

EXAMPLE 2

In a second non-limiting example, the user defines the limit as 60 Gy and the resultant threshold value is again 63 Gy. In this example, however, the target volume exceeding 60 Gy is 10% of the volume with 1.9% of the volume receiving more than 63 Gy. In this case, the adaptive limit can be limited by the maximum fraction for the adaptive constraint (for example, 0.2%). Accordingly, a dose limit can be calculated so that the fraction receiving more than the dose limit will be the maximum fraction of the adaptive constraint. In this case, if 0.2% of the volume receives 68 Gy, then the constraint could be applied to regions where the dose exceeds 68 Gy.

Figure 2:
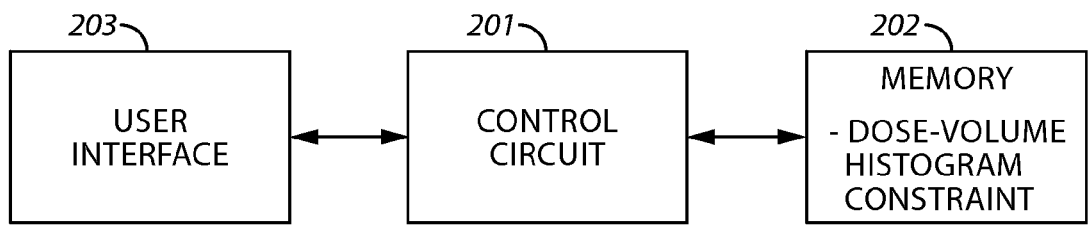
FIG. 2 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

This apparatus 200 can generally comprise, for example, an arc-radiation treatment-planning apparatus, an intensity-modulated radiation-treatment planning apparatus, or the like. This apparatus 200 can generally comprise, in part, a control circuit 201 that operably couples to a memory 202 and a user interface 203. Those skilled in the art will recognize and appreciate that such a control circuit 201 can comprise a fixed-purpose hard-wired platform or can comprise a partially or wholly programmable platform. Such architectural options are well known and understood in the art and require no further description here.

The memory 202 can serve, for example, to store digital versions of the aforementioned dose-volume histogram constraint(s), one or more corresponding dose-volume histograms, and so forth. This memory 202 can also serve to store, if desired, computer operating instructions (when, for example, the control circuit 201 comprises, in whole or in part, a programmable platform such as a microprocessor or the like). It will also be understood that the memory component shown can comprise a plurality of memory elements or can be comprised of a single memory element (as is suggested by the illustration).

The user interface 203 can comprise one or more components that serve to present information to a user and/or that receive input from the user. This can include, but is certainly not limited to, a color video display in conjunction with a cursor control and select mechanism such as a computer mouse, trackball, or the like. Generally speaking, and by one approach, this user interface 203 comprises a dose-volume histogram-based user interface in that the interface will support and readily permit both displaying a dose-volume histogram to a user and permitting that user to denote, at the least, the placement of at least one dose-volume histogram constraint.

The control circuit 201 is operably configured (for example, via corresponding programming as will be well understood by those skilled in the art) to carry out one or more of the steps, actions, or functionalities described herein. This can specifically comprise, for example, configuring the control circuit 201 to recover from the memory 202 a first dose-volume histogram constraint as pertains to controlling localized excessive-radiation dosage with respect to a particular treatment volume, automatically determining whether to supplement the first dose-volume histogram constraint, and, upon making this determination, automatically supplementing the first dose-volume histogram constraint using an adaptive dose-volume histogram constraint.

Those skilled in the art will recognize and understand that such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

By one approach, the described adaptive component can be viewed as comprising two parts. The first part comprises changing a lower dose value for lower constraints or correspondingly changing upper dose values for upper constraints. The second part comprises a limited region of allowed values for the affected volume fraction. Essentially, these teachings accommodate and leverage the placement of a sufficiently-high penalty on a very small fraction of the overall volume. If the affected volume is not decreased when small volume fractions have large deviations from one or more preferred values, then either the small region has too small a weight and is not affected or a larger region in the same state would have too high a penalty. These situations are usually not known in advance and may even change during optimization. These teachings readily support handling both situations essentially without user interference.

So configured, these teachings are well suited for use with, and for leveraging, known uses of dose-volume histogram constraints to control hot and cold spots. Generally speaking, these teachings will permit the use of traditional approaches in these regards unless and until it becomes apparent that the constraint(s) determined by such approaches are inadequate. When appropriate, these teachings then supplement the use of traditional constraints with an adaptive constraint that essentially only penalizes for a predefined lowest proportion (and/or predefined highest proportion) of the dose-volume histogram curve.

Those skilled in the art will appreciate that these benefits are attainable in a transparent manner. By one approach, for example, this adaptive response automatically occurs when and as the user sets a dose % constraint at a range boundary (such as 0% or 100%). In effect, these teachings will accommodate and leverage interpreting such a setting as identifying a hot or cold spot contribution.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
    at a radiation-treatment planning apparatus:
        providing a first dose-volume histogram constraint as pertains to controlling localized excessive-radiation dosage with respect to a particular treatment volume;
        automatically determining whether to supplement the first dose-volume histogram constraint by determining whether a user has specified such supplementation via placement of at least one dose-volume histogram constraint using a corresponding user interface; and
        upon determining to supplement the first dose-volume histogram constraint, automatically supplementing the first dose-volume histogram constraint using an adaptive dose-volume histogram constraint.

2. The method of claim 1 wherein the radiation-treatment planning apparatus comprises an arc-radiation-treatment planning apparatus.

3. The method of claim 1 wherein the radiation-treatment planning apparatus comprises an intensity-modulated radiation-treatment planning apparatus.

4. The method of claim 1 wherein providing a first dose-volume histogram constraint comprises determining the first dose-volume histogram constraint by at least one of penalizing and emphasizing a corresponding objective function when at least one identified volume fraction is exceeded at a given radiation dosage.

5. The method of claim 1 wherein determining whether a user has specified such supplementation via placement of at least one dose-volume histogram constraint using a corresponding user interface comprises determining whether the user has placed the at least one dose-volume histogram constraint such that the at least one dose-volume histogram constraint corresponds to a volume fraction at a range boundary.

6. The method of claim 5 wherein the range boundary comprises at least one of 0% and 100%.

7. The method of claim 1 further comprising:
determining the adaptive dose-volume histogram constraint.

8. The method of claim 1 wherein automatically supplementing the first dose-volume histogram constraint using an adaptive dose-volume histogram constraint comprises further penalizing no more than a predefined volume fraction that is smaller than the volume fraction that is constrained by the first dose-volume histogram constraint.

9. The method of claim 8 wherein the predefined volume fraction is no more than about 1.0% of the treatment volume.

10. The method of claim 9 wherein the predefined volume fraction is no more than about 0.1% of the treatment volume.

11. An apparatus comprising:
a dose-volume histogram-based user interface;
a memory; and
a control circuit operably coupled to the dose-volume histogram-based user interface and the memory and being configured to:
recover from the memory a first dose-volume histogram constraint as pertains to controlling localized excessive-radiation dosage with respect to a particular treatment volume;
automatically determine whether to supplement the first dose-volume histogram constraint by determining whether a user has specified such supplementation via the dose-volume histogram-based user interface via placement of at least one dose-volume histogram constraint using the user interface; and
upon determining to supplement the first dose-volume histogram constraint, automatically supplement the first dose-volume histogram constraint using an adaptive dose-volume histogram constraint.

12. The apparatus of claim 11 wherein the apparatus comprises an arc-radiation-treatment planning apparatus.

13. The apparatus of claim 11 wherein the apparatus comprises an intensity-modulated radiation-treatment planning apparatus.

14. The apparatus of claim 11 wherein the control circuit is configured to provide a first dose-volume histogram constraint by determining the first dose-volume histogram constraint by at least one of penalizing and emphasizing a corresponding objective function when at least one identified volume fraction is exceeded at a given radiation dosage.

15. The apparatus of claim 11 wherein the control circuit is configured to determine whether a user has specified such supplementation via placement of at least one dose-volume histogram constraint using the user interface by determining whether the user has placed the at least one dose-volume histogram constraint such that the at least one dose-volume histogram constraint corresponds to a volume fraction at a range boundary.

16. The apparatus of claim 15 wherein the range boundary comprises at least one of 0% and 100%.

17. The apparatus of claim 11 wherein the control circuit is further configured to determine the adaptive dose-volume histogram constraint.

18. The apparatus of claim 11 wherein the control circuit is configured to automatically supplement the first dose-volume histogram constraint using an adaptive dose-volume histogram constraint by further penalizing no more than a predefined volume fraction that is smaller than the volume fraction that is constrained by the first dose-volume histogram constraint.

19. The apparatus of claim 18 wherein the predefined volume fraction is no more than about 1.0% of the treatment volume.

20. The apparatus of claim 19 wherein the predefined volume fraction is no more than about 0.1% of the treatment volume.

* * * * *